United States Patent
Lingeman et al.

(10) Patent No.: US 9,775,633 B2
(45) Date of Patent: *Oct. 3, 2017

(54) MEDICAL DEVICE HANDLES AND RELATED METHODS OF USE

(71) Applicant: Boston Scientific Scimed, Inc., Maple Grove, MN (US)

(72) Inventors: John Lingeman, Plainfield, IN (US); Jennifer Keeler, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/078,648

(22) Filed: Mar. 23, 2016

(65) Prior Publication Data

US 2016/0199133 A1    Jul. 14, 2016

Related U.S. Application Data

(63) Continuation of application No. 14/642,479, filed on Mar. 9, 2015, now Pat. No. 9,320,531, which is a
(Continued)

(51) Int. Cl.
*A61B 18/18* (2006.01)
*A61B 17/22* (2006.01)
(Continued)

(52) U.S. Cl.
CPC ...... *A61B 17/22012* (2013.01); *A61B 17/221* (2013.01); *A61B 18/22* (2013.01);
(Continued)

(58) Field of Classification Search
CPC . A61B 17/22012; A61B 17/221; A61B 18/22; A61B 18/26; A61B 2017/00353;
(Continued)

(56) References Cited

U.S. PATENT DOCUMENTS 5,108,406 A    4/1992  Lee
5,562,678 A   10/1996  Booker
(Continued)

*Primary Examiner* — George Manuel
(74) *Attorney, Agent, or Firm* — Bookoff McAndrews, PLLC

(57) ABSTRACT

A device may include a sheath including a lumen, a distal end, and a proximal end. The device may further include an end-effector unit and an elongate member connected to the end-effector unit. The end-effector unit and the sheath may be movable relative to each other to achieve a first state of the end-effector unit and a second state of the end-effector unit. Moreover, the medical device may include a handle having a first handle portion connected to the proximal end of the sheath, a second handle portion connected to the proximal end of the elongate member, and a compliant member longitudinally aligned with the sheath between the first handle portion and the second handle portion. The first and second handle portions may be configured such that relative movement of the first and second handle portions causes the end-effector to move between the first and second states.

20 Claims, 10 Drawing Sheets

Related U.S. Application Data continuation of application No. 13/558,505, filed on Jul. 26, 2012, now Pat. No. 9,005,196.

(60) Provisional application No. 61/524,073, filed on Aug. 16, 2011.

(51) Int. Cl.
| | |
|---|---|
| *A61B 18/22* | (2006.01) |
| *A61B 17/221* | (2006.01) |
| *A61B 17/00* | (2006.01) |
| *A61B 18/00* | (2006.01) |
| *A61B 18/26* | (2006.01) |
| *A61B 17/29* | (2006.01) |

(52) U.S. Cl.
CPC ......... *A61B 18/26* (2013.01); *A61B 2017/008* (2013.01); *A61B 2017/0038* (2013.01); *A61B 2017/00353* (2013.01); *A61B 2017/00371* (2013.01); *A61B 2017/00469* (2013.01); *A61B 2017/22038* (2013.01); *A61B 2017/2924* (2013.01); *A61B 2017/2946* (2013.01); *A61B 2018/0091* (2013.01); *A61B 2018/00916* (2013.01); *A61B 2217/005* (2013.01)

(58) Field of Classification Search
CPC .. A61B 2017/00371; A61B 2017/0038; A61B 17/00469; A61B 2017/008; A61B 2017/22038; A61B 2017/2924; A61B 2017/2946; A61B 2018/0091; A61B 2018/00916; A61B 2217/005
See application file for complete search history.

(56) References Cited

U.S. PATENT DOCUMENTS

| | | | |
|---|---|---|---|
| 7,608,083 B2* | 10/2009 | Lee | ............ A61B 17/0469 606/1 |
| 2008/0300590 A1 | 12/2008 | Horne et al. | |

* cited by examiner

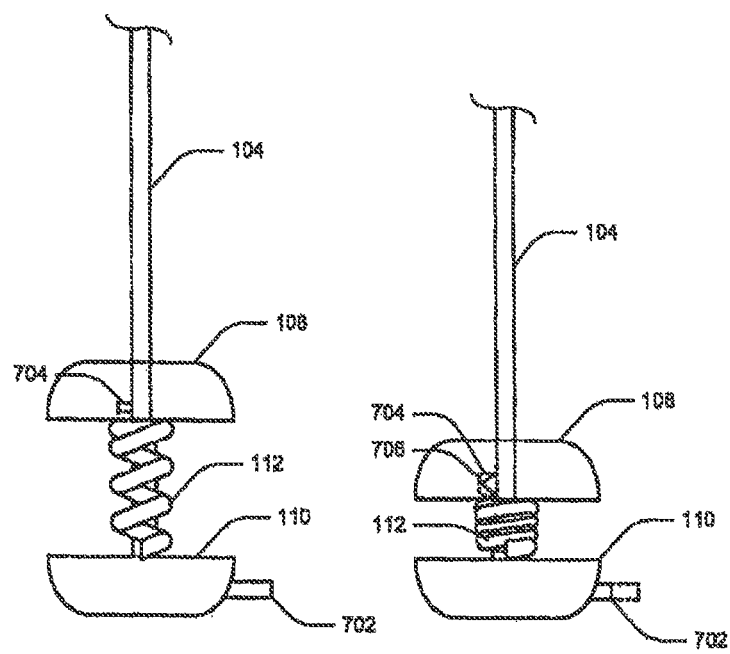

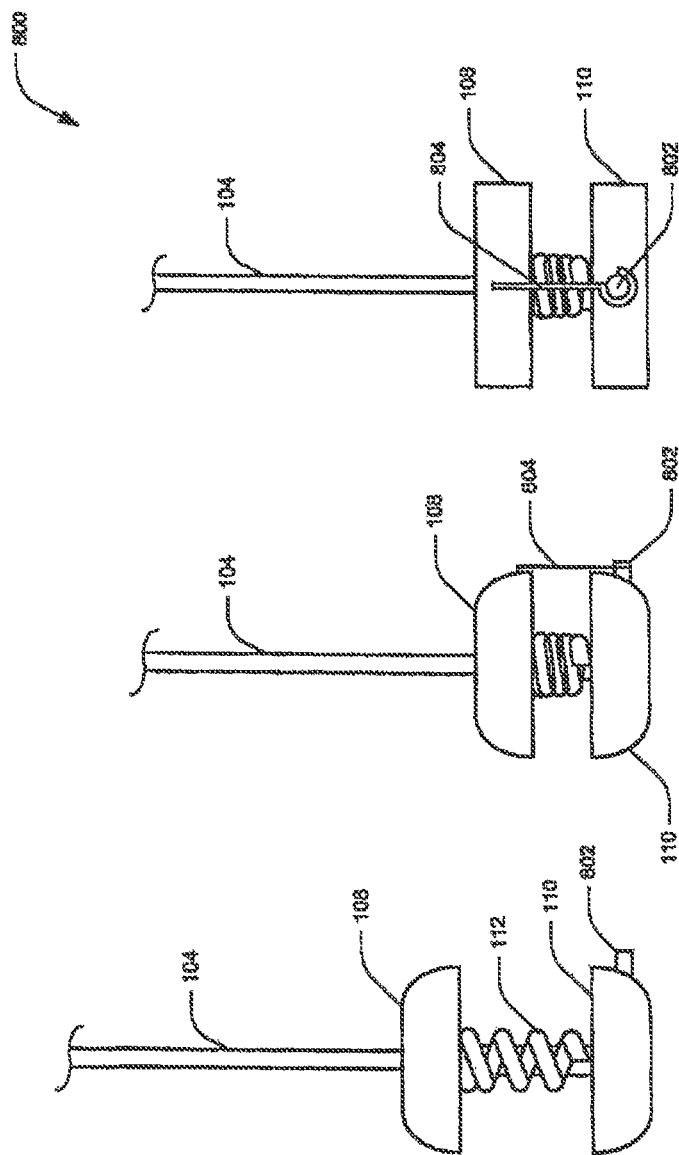

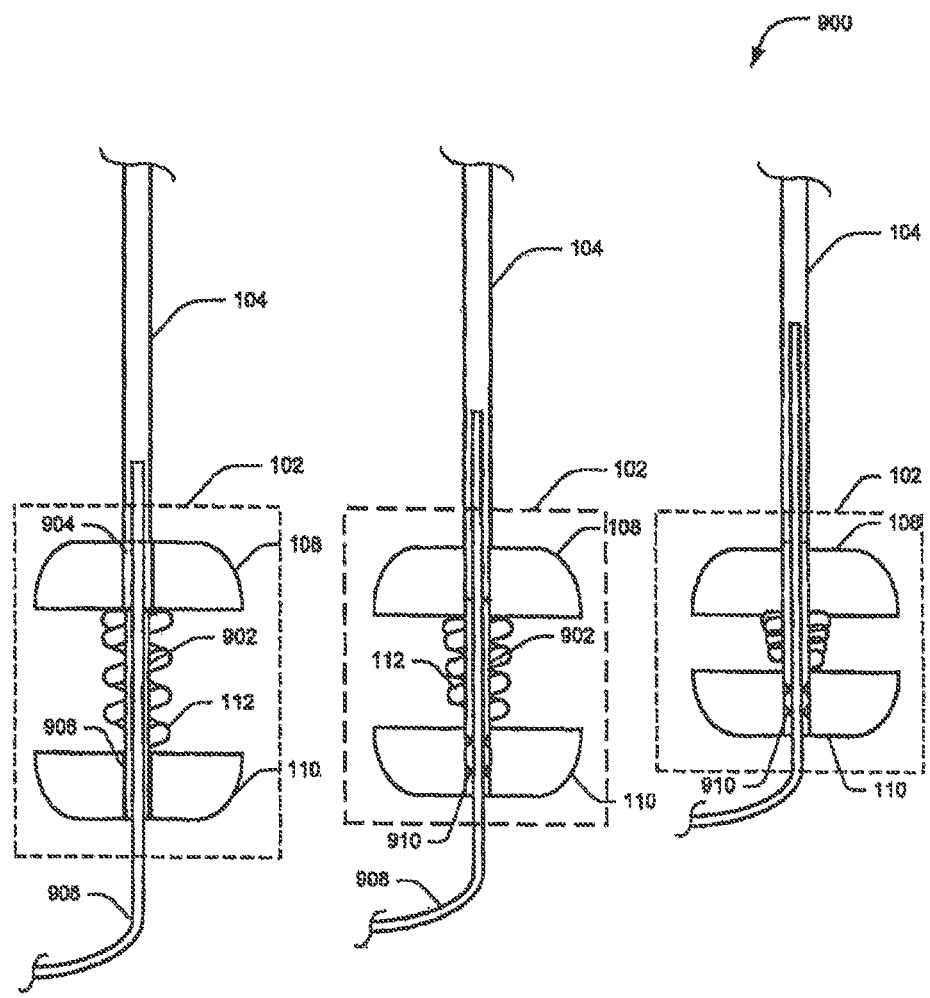

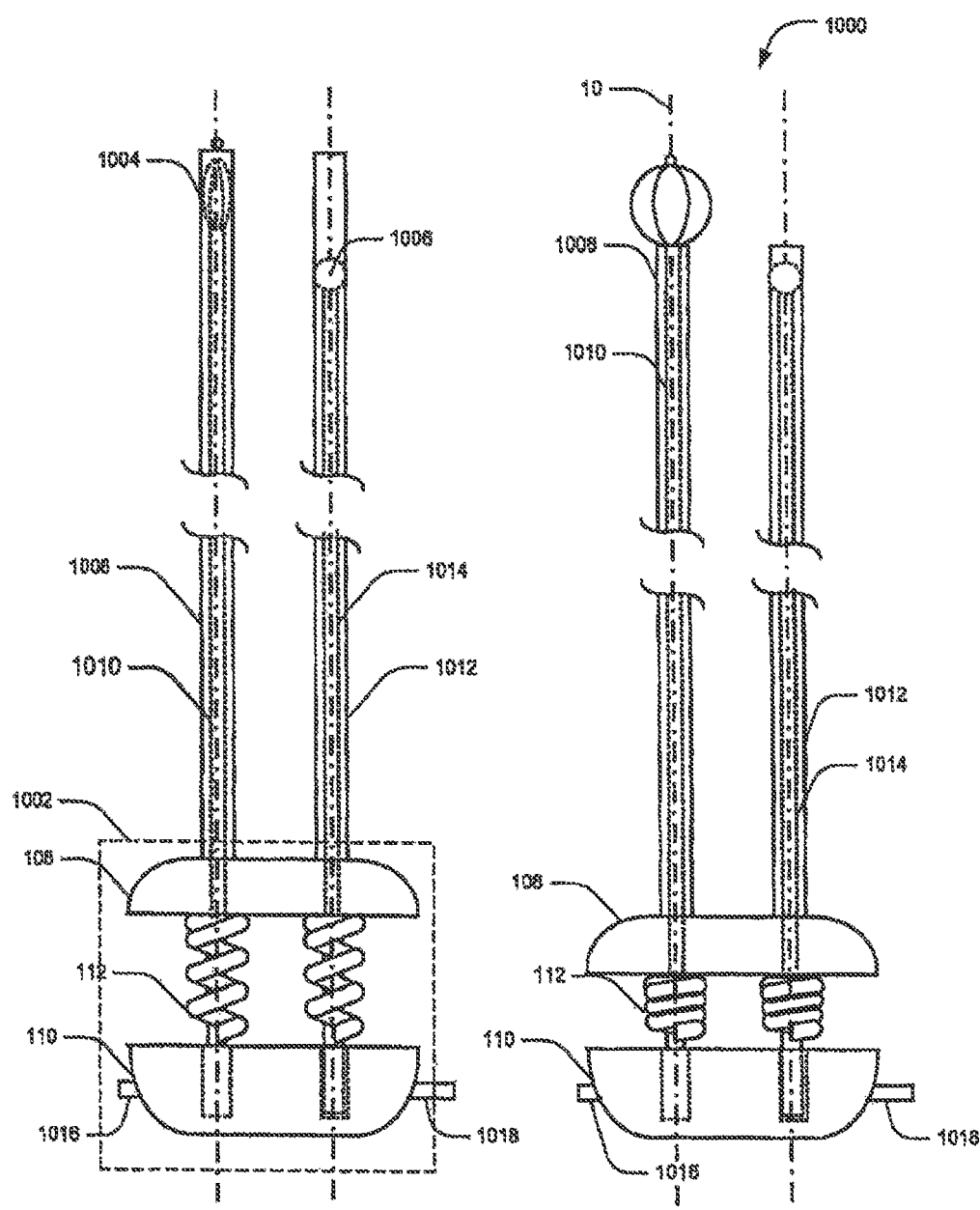

MEDICAL DEVICE HANDLES AND RELATED METHODS OF USE

CROSS-REFERENCE TO RELATED APPLICATIONS

This application is a Continuation Application of U.S. patent application Ser. No. 14/642,479, filed Mar. 9, 2015, which is a continuation of U.S. patent application Ser. No. 13/558,505, filed Jul. 26, 2012 (now U.S. Pat. No. 9,005,196) which claims the benefits of priority under 35 U.S.C. §§119-120 to U.S. Provisional Application No. 61/524,073, filed on Aug. 16, 2011, all of which are incorporated herein by reference in their entireties.

FIELD OF THE INVENTION

This disclosure relates to handle assemblies for medical devices and related methods of use. More particularly, embodiments of the disclosure relate to improved handles for actuating and positioning medical implements by a single hand of an operator.

BACKGROUND OF THE INVENTION

Minimally invasive surgical devices, such as endoscopes, laparoscopes, and retrieval devices can provide access to remote surgical sites within a human body through body openings, cavities, or tracts. Such surgical devices may include elongate portions that are maneuverable in the openings and that allow an operator to simultaneously view and operate at the remote site. In the field of urology, medical retrieval devices, such as collapsible baskets, graspers and the like, are used to retrieve various foreign or biological materials, such as kidney stones, urinary calculi, and choleliths, from within a body. In certain urological procedures, the retrieval device is used to immobilize kidney stones relative to a laser fiber. Lithotripsy then fragments the stones for retrieval and removal by the retrieval device.

Medical retrieval devices typically include a sheath and an object-engaging unit, such as a basket, that is moveable relative to the sheath from a collapsed state within the sheath to another state in which the unit extends past the distal end of the sheath. The sheath typically extends from a handle, located at the proximal end of the sheath to the object-engaging unit which is located at the distal end of the sheath. As such, the term "proximal end" refers to the end away from the patient and the term "distal end" refers to the end near the patient and that goes into the patient. The handle often includes a mechanism for actuating the object-engaging unit in order to move the object-engaging unit between the collapsed and extended, expanded states.

During a urological procedure, a physician moves the distal end of the medical retrieval device in relation to the distal end of an insertion device, e.g., a ureteroscope. This may be accomplished by gripping the sheath just proximal to the point where the retriever sheath is introduced into a channel within the ureteroscope. As the physician operates the ureteroscope and positions the sheath of the retrieval device, an assistant is required to actuate the handle at the physician's direction to retrieve foreign material.

In procedures that utilize a laser fiber and a retrieval device, the physician must carefully hold and reposition the two items relative to each other and to the ureteroscope. Currently, an operator must manipulate and actuate each device independently or with the assistance of another operator. Such procedures can become time consuming and cumbersome.

In light of the foregoing, there is a need for an improved handle for a medical retrieval device that allows for the device to be introduced, positioned, and actuated by a single hand of an operator.

SUMMARY OF THE INVENTION

Embodiments of the disclosure are directed to improved handles for medical devices, and related methods of use that obviate one or more of the limitations of the prior art medical device handles.

One embodiment of the disclosure is directed to a medical device. The device may include a sheath including a lumen, a distal end, and a proximal end. The device may further include an end-effector unit and an elongate member connected to the end-effector unit and extending proximally from the end-effector unit within the lumen of the sheath. The end-effector unit and the sheath may be movable relative to each other to achieve a first state of the end-effector unit and a second state of the end-effector unit. Moreover, the medical device may include a handle having a first handle portion connected to the proximal end of the sheath, a second handle portion connected to the proximal end of the elongate member, and a compliant member longitudinally aligned with the sheath between the first handle portion and the second handle portion to hold the first handle portion and the second handle portion in a spaced apart position. The first and second handle portions may be configured such that relative movement of the first handle portion towards the second handle portion causes the end-effector to move between the first state and the second state.

In various embodiments, the medical device may include one or more of the following additional features: the first handle portion may be distal of the second handle portion; the second handle portion may be distal of the first handle portion; the handle may include a locking mechanism to secure the first and second handle portions after the first handle portion is moved toward the second handle portion; the end-effector unit may be a self-expandable basket having a plurality of legs; in the first state, the end effector unit may be within the lumen and in the second state the end-effector unit may extend from the distal end of the sheath; in the first state, the end-effector unit may extend from the distal end of the sheath and in the second state the end-effector unit may be within the lumen; the basket may be collapsed when the end-effector unit is in the first state and expanded when the end-effector unit is in the second state; the basket may be collapsed when the end-effector unit is in the second state and expanded when the end-effector unit is in the first state; a distal end of the elongate member may be connected to a proximal end of the end-effector unit; the compliant member may define a lumen and may be made of a material that compresses under force and returns to its original state once the force is removed; the elongate member may be at least one of a tube, a shaft, a wire, a coil, or a cable connected to a proximal end of the end-effector unit; the handle may include an electrical connector for delivering electrical current to the end-effector unit; one of the first handle portion and the second handle portion may include geometric features for receiving one or more fingers of an operator and the medical device may include two or more distinct end-effector units, each separately actuatable by the handle.

According to another embodiment, a medical device may include a sheath having a lumen, a distal end, and a proximal end may be provided. The medical device may further include a handle having a first handle portion connected to the proximal end of the sheath, a second handle portion including a hole, and a tube disposed between the first and second handle portions. The tube may include a distal end, a proximal end, and a lumen extending in between. The distal end of the tube may be slidably disposed within the sheath, and the proximal end of the tube may be connected to the second handle portion and be in communication with the hole in the second handle portion. The handle may further include a compliant member positioned around the tube between the first handle portion and the second handle portion to keep them in a spaced apart position. The lumen of the tube may be configured to receive a device, and wherein moving the second handle portion towards the first handle portion may cause the device to be pushed towards the distal end of the sheath.

In various embodiments, the medical device may include one or more of the following additional features: a portion of the medical device may further include an engaging member that selectively protrudes from a surface of a portion of the medical device; the engaging member may protrude when the second handle portion is pushed towards the first handle portion and may retract when the first and second handle portion returns to the spaced apart position.

A further aspect of the present disclosure provides a method for operating a medical device to perform an operation in a body. The method may include the step of advancing a medical device to a position within a body. The medical device may include a sheath including a lumen, a distal end, and a proximal end. The device may further include an end-effector unit and an elongate member connected to the end-effector unit and extending proximally from the end-effector unit within the lumen of the sheath. The end-effector unit and the sheath may be movable relative to each other to achieve a first state of the end-effector unit when the end-effector unit is within the lumen and a second state of the end-effector unit when the end-effector unit extends from the distal end of the sheath. The device may further include a handle having a first handle portion connected to the proximal end of at least one of the sheath, a second handle portion connected to the proximal end of the elongate member, and a compliant member longitudinally positioned between the first handle portion and the second handle portion to keep the handle portions in a spaced apart position. The method may further include the steps of grasping the handle with a hand of an operator in a position to push one of the first and second handle portions towards the other, and pushing a handle portion towards the other to selectively actuate the end-effector unit between the first state and the second state.

In various embodiments, the method may further include the additional features of locking the first and second handle portions to prevent relative movement between the two handle portions.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate embodiments of the disclosure and together with the description, serve to explain the principles of the invention.

FIG. 7A is a schematic view of a handle of the medical device of FIG. 1, illustrating a locking mechanism in the open position according to one embodiment of the present disclosure.

FIG. 7B is a schematic view of the handle of FIG. 7A illustrating the locking mechanism in a closed position.

FIG. 8A is a schematic view of a handle of the medical device of FIG. 1, illustrating a locking mechanism in the open, unlocked position according to another embodiment of the present disclosure.

FIG. 8B is a schematic view of the handle of FIG. 8A illustrating the locking mechanism in a closed, locked position.

FIG. 8C is a side view of the handle of FIG. 8B illustrating the locking mechanism in a closed, locked position.

FIGS. 9A-9C is a schematic view of a medical device according to another embodiment of the present disclosure.

FIG. 10A is a schematic view of a medical device housing multiple tools.

FIG. 10B illustrates the medical device of FIG. 10A in an actuated state.

DESCRIPTION OF THE EMBODIMENTS

Reference will now be made in detail to embodiments of the disclosure, examples of which are illustrated in the accompanying drawings. Wherever possible, the same reference numbers will be used throughout the drawings to refer to the same or like parts.

Figure 1:
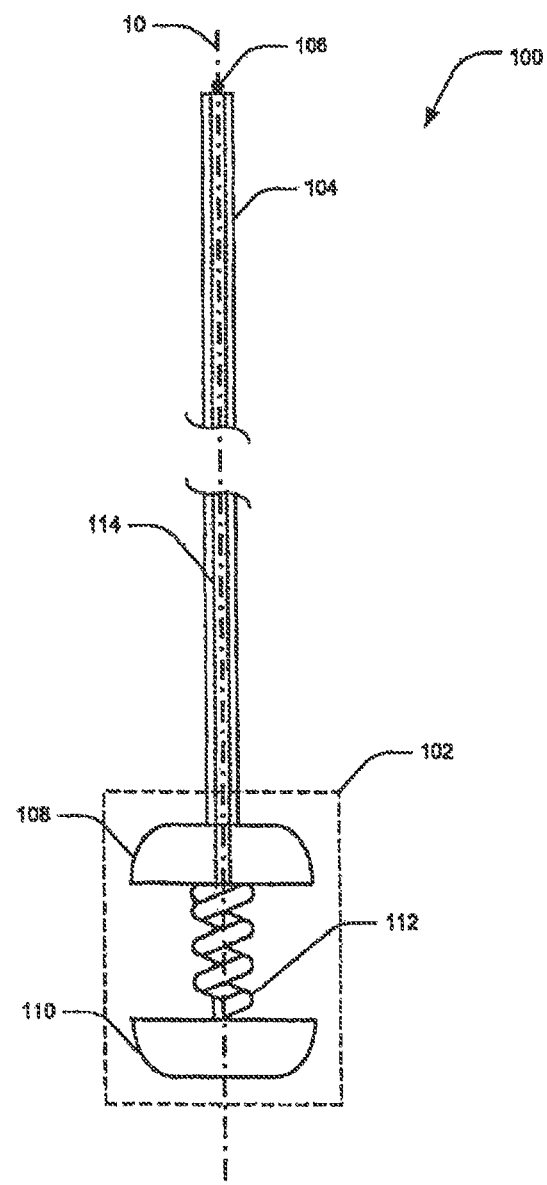
FIG. 1 is a schematic view of a medical device with a collapsed end-effector and a handle in a spaced apart position according to an embodiment of the present disclosure.
Figure 2:
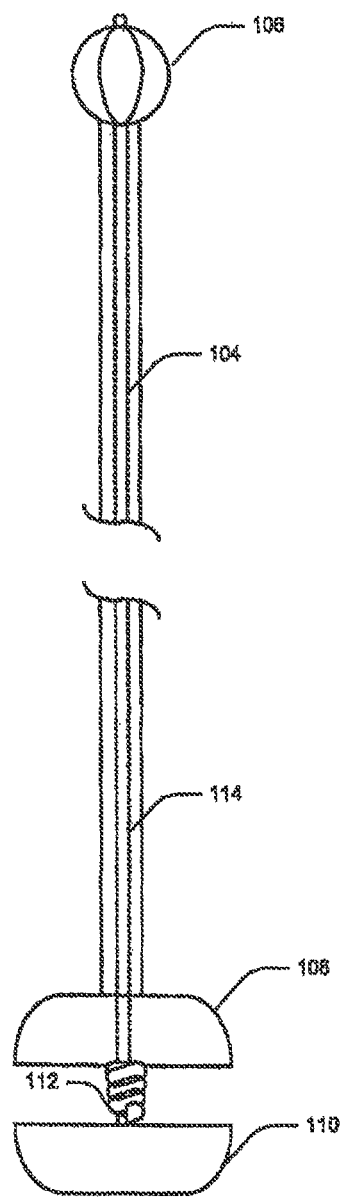
FIG. 2 illustrates the medical device of FIG. 1 in an actuated state according to one embodiment of the present disclosure.

Referring to FIGS. 1 and 2, one embodiment of a medical device 100 includes a handle 102, a sheath 104, and an end-effector unit 106 all extending along a longitudinal axis 10. The sheath 104 may be flexible, and it may include one or more internal lumens for receiving one or more end-effectors, such as the end-effector unit 106, imaging devices, etc. As will be described in more detail below, the end-effector unit 106 and the sheath 104 are movable relative to each other in order to achieve a first collapsed state of the end-effector unit 106 (seen in FIG. 1) in which the end effector unit 106 is collapsed within the lumen of the distal end of the sheath 104 and a second state in which the end-effector unit 106 extends from the distal end of the sheath 104 and expands to an operable or actuated state (seen in FIG. 2).

The end-effector unit 106 may include a basket, a grasper, pincers, snares, or any other retrieval or grasping device. In some embodiments, the end effector unit 106 may be self-expandable. Moreover, the end-effector unit 106 may include a device for performing a therapeutic or diagnostic operation in a body such as a urological, endoscopic, or other such operation. For example, the end-effector unit 106 may include an ablation probe, cautery, or a lithotriptor without departing from the scope of the disclosure. In the figures presented here, as an example, the end-effector unit 106 is illustrated as a basket, such as a self-expandable percutaneous nephrolithotomy (PCNL) basket having several legs. The basket may be made of any memory metal such as nitinol.

The handle 102 further includes a first handle portion and a second handle portion such as an upper handle portion 108 and a lower handle portion 110, separated by a compliant member 112 longitudinally aligned along the longitudinal axis 10. Here, the first handle portion is illustrated as the upper handle portion 108 (at the distal end of the handle) while the second handle portion is illustrated as the lower handle portion 110 (at the proximal end of the handle). It will be understood, however, that the handle portions may be interchangeably illustrated in other embodiments. For example, the first handle portion may be the lower handle portion 110 and the second handle portion may be the upper handle portion 108 in other embodiments.

The compliant member 112 may be configured as a tube or sleeve defining a lumen through which an elongate member 114 or the sheath 104 may extend. Further, this compliant member 112 may be a spring element such as a helical spring, an elastic sleeve, or any other such material that compresses under force and returns to its original state once the force is removed. The compliant member 112 may be configured to exert forces against the upper and lower handle portions 108, 110, to bias them away from one another, holding the handle portions in a naturally spaced apart position.

In this embodiment, the proximal end of the sheath 104 is attached to the upper handle portion 108, while the lower handle portion 110 is attached to the proximal end of the elongate member 114. The elongate member 114 may be a flexible member, disposed within the lumen of the sheath 104, extending proximally from the end-effector unit 106 to the lower handle portion 110. Structure of the elongate member 114 may be in the form of a flexible shaft, coil, cable, or wire.

Attachment of the sheath 104 and the elongate member 114 to the upper and lower handle portions 108, 110 may be accomplished using a number of different permanent and temporary connection techniques. Examples of permanent techniques may include welding, soldering, gluing, or crimping the proximal end of the sheath 104 or the elongate member 114 with contacting portions of the upper or the lower handle portion 108, 110. An example of temporary attachment may include screw-fit or snap-fit connections. For example, the upper and lower handle portions 108, 110 may include unthreaded or threaded annular protrusions or grooves (not shown) around which or into which the proximal end of the sheath 104 or the elongate member 114 may be attached. It will be understood that these connection techniques may be utilized to attach these parts or any other parts of the medical device in this embodiment or in other embodiments, without departing from the scope of the present invention. For example, these techniques may be utilized to attach the sheath 104 to the lower handle portion 110 and the elongate member 114 to the upper handle portion 108 in other embodiments.

Although the depicted embodiment illustrates a single elongate member 114, those of ordinary skill in the art will appreciate that any suitable number of elongate members 114 may extend from the handle 102 to the end-effector unit 106. Further, the diameter of the elongate member 114 and the sheath 104 may be relatively smaller than the diameter of the upper handle portion 108 and the lower handle portion 110. Depending on the application, the diameter of the sheath 104 and elongate member 114 may vary (e.g., smaller for narrower body cavities), however, the handle portions 108, 110 may have a relatively standard size (depending on the palm size of the operator). For example, the handle 102 may have a size that comfortably fits in the palm of an operator.

Actuating the end-effector unit 106 between a collapsed state (FIG. 1) and an expanded state (FIG. 2) may be accomplished by pushing one handle portion (upper, lower) towards the other, or both towards each other against the force applied by the compliant member 112. In the expanded state, the end-effector unit 106 may retrieve an object from within the body, or perform any desired function.

Figure 3:
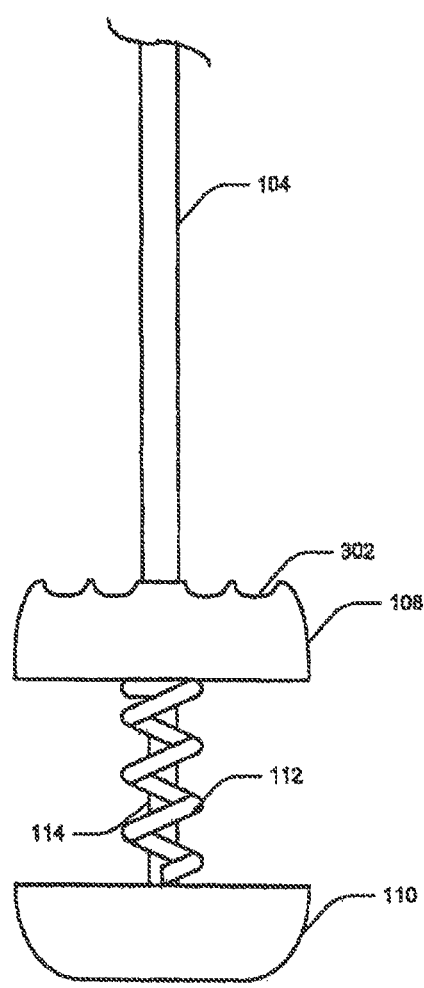
FIG. 3 illustrates a medical device with finger grooves in a handle according to an embodiment of the present disclosure.

The handle 102 is gripped in the palm of an operator, and may include geometric features, such as finger grooves in the upper handle portion 108, to assist in handling the medical device 100. FIG. 3 illustrates one such embodiment in which the upper handle portion 108 includes four separate grooves 302 for a user's fingers. It will be understood that FIG. 3 is merely exemplary and that other groove designs may also be contemplated. For example, the upper handle portion may include two grooves (one on each side of the sheath). Each groove may then accommodate two fingers. Moreover, the lower handle portion may include a groove for the operator's thumb. Other geometries, such as rings for receiving the operator's fingers may also be considered. With reference to FIGS. 1-3, it will be understood that the upper handle portion 108 and the lower handle portion 110 may be spaced apart at a distance that allows an operator to hold both the handle portions in a single hand and bring the handle portions together with ease when actuating the end-effector unit 106.

In the medical device 100, the end-effector unit 106 advances out of the sheath 104 when the handle portions are brought together, and withdraws into the sheath 104 when the handle portions are spaced apart. As alluded to above, the end effector unit 106 may be configured to self-expand when it is released from the constraints of the sheath 104. In addition, the end-effector unit 106 may be configured to return to a compressed state as it is being withdrawn into the sheath 104.

Figure 4:
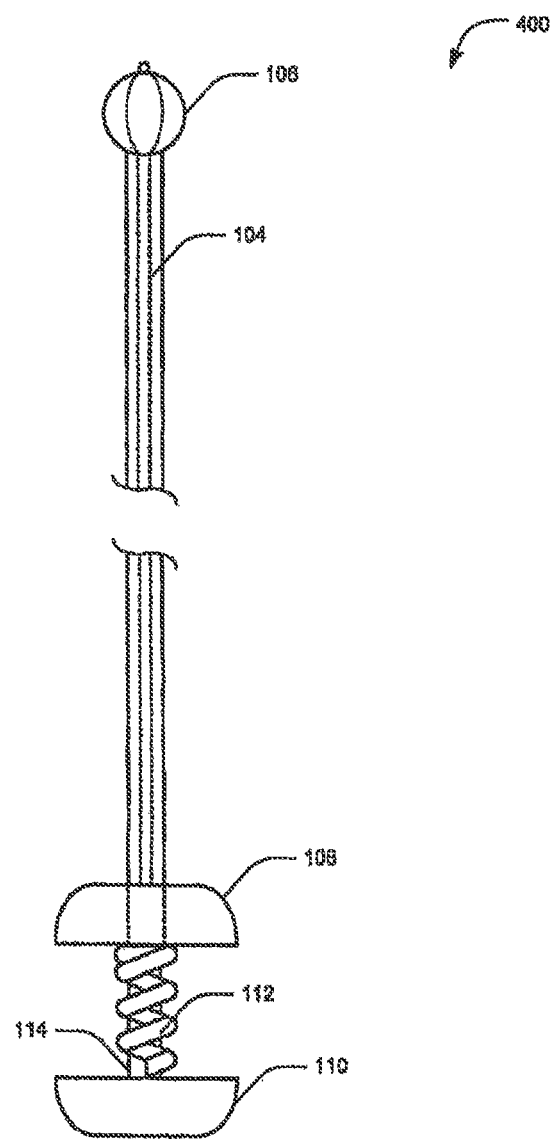
FIG. 4 is a schematic view of a medical device with a handle according to another embodiment of the present disclosure.
Figure 5:
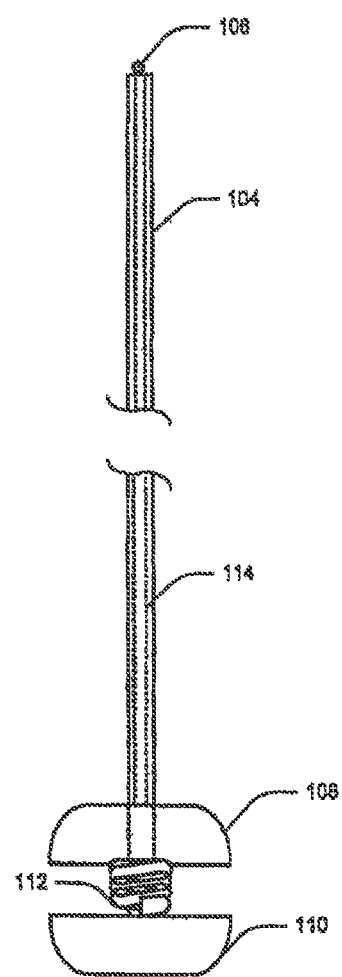
FIG. 5 illustrates the medical device of FIG. 4 in an actuated state.
Figure 6:
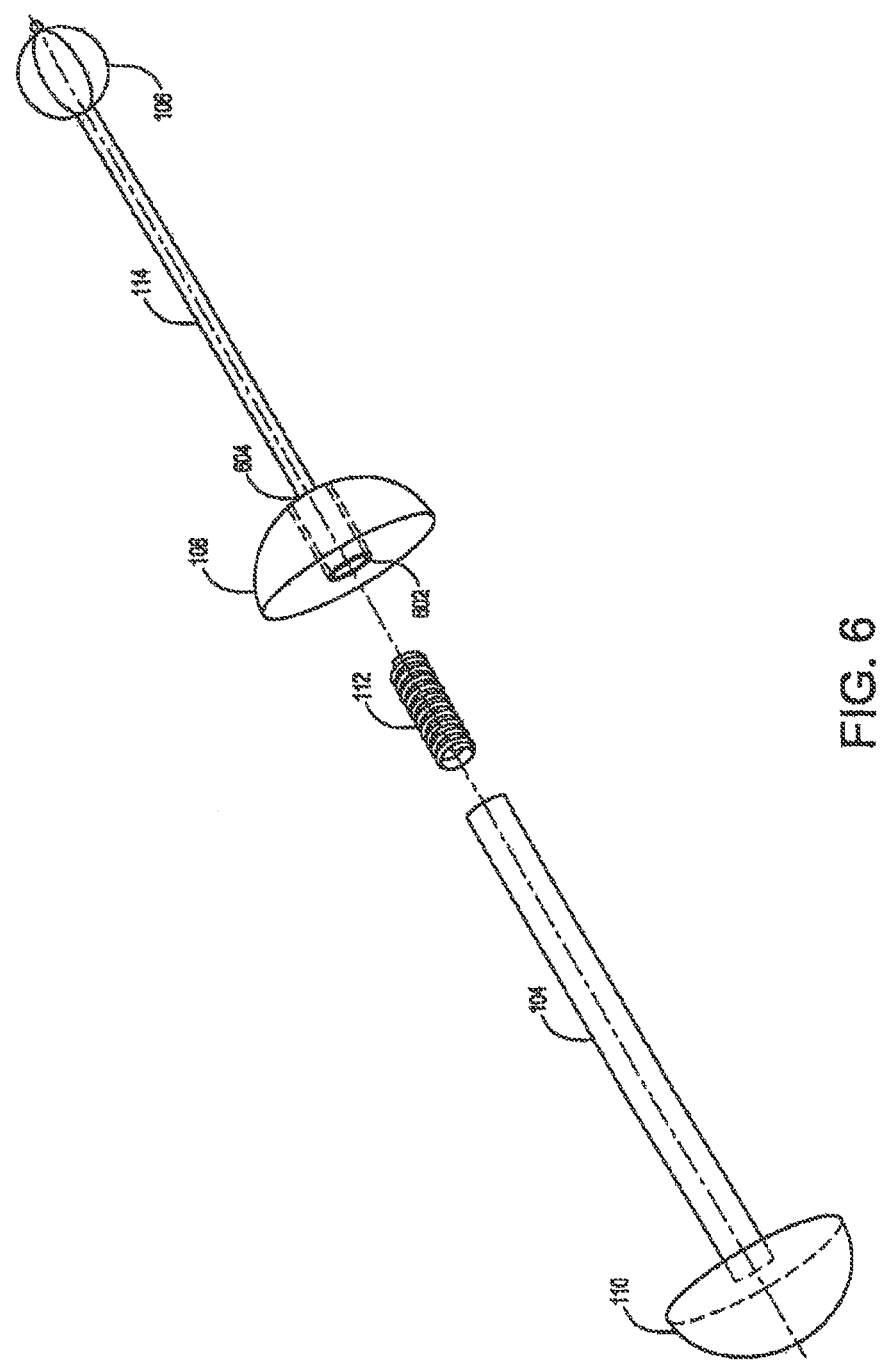
FIG. 6 is an exploded view of the medical device of FIG. 4.

FIGS. 4, 5, and 6 illustrate another embodiment of the medical device 400 in which the end-effector unit 106 is in the extended and expanded operable state when the handle portions are spaced apart (FIG. 4) and in the withdrawn and collapsed state when the handle portions are brought together (FIG. 5). FIG. 6 illustrates an exploded view of the medical device of FIGS. 4 and 5. To achieve this configuration, the sheath 104 may be attached to the lower handle portion 110, instead of the upper handle portion 108, while the elongate member 114 may be connected to the upper handle portion 108. It will be understood that in this embodiment the first handle portion is embodied as the lower handle portion 110 (at the proximal end of the handle), while the second handle portion is embodied as the upper handle portion 108 (at the distal end of the handle).

The upper handle portion 108 may include a hollow ring 602 (shown in FIG. 6) through which sheath 104 may pass. The hollow ring 602 may have a thickness comparable to the thickness of the sheath 104 so that the sheath 104 passes through the upper handle portion 108 with relative ease and without excessive friction. The upper handle portion 108 may further include a solid central portion 604 where the elongate member 114 is attached. FIG. 6 is an isometric view of the medical device clearly depicting the hollow ring 602 and the central portion 604. The hollow ring 602 allows unrestricted motion between the sheath and the upper handle portion 108.

When the upper handle portion 108 is brought towards the lower handle portion 110 against the force of the compliant member, the elongate member 114 may be pulled proximally into the lumen of the sheath 104, thereby collapsing and retracting the end-effector unit 106 into the sheath 104. Alternatively, when the lower handle portion 110 is pushed towards the upper handle portion 108, the sheath 104 may extend distally, covering the exposed end-effector unit 106, thereby collapsing it.

In the embodiment described with reference to FIGS. 4-6, the compliant member 112 may be present within the sheath 104 (preferably at the proximal end of the sheath. Here, the compliant member 112 may not include a lumen or be shaped as a sleeve. Instead, the complaint member 112 may have any shape which is insertable into the sheath 104. The length and compressibility of the compliant member 112 may be configured, such that there is sufficient distance between the upper handle portion 108 and the lower handle portion 110 in the spaced apart position and such that compression of the handle portions substantially collapses and retracts the end-effector unit 106 into the sheath 104.

To lock the end-effector unit 106 in a particular state, such as an expanded state in the first embodiment (FIG. 2) or a collapsed state in the second embodiment (FIG. 5), the handle 102 may include a locking mechanism. It will be understood that various locking mechanism may be used, as known in the art, without departing from the scope of the present disclosure. FIGS. 7-8 illustrate two such locking mechanisms.

FIGS. 7A and 7B illustrate a locking mechanism applicable to the first embodiment of the medical device 100. It will be understood, however, that with minor modification in the design, this locking mechanism will be suitable for the second embodiment of the medical device as well. As illustrated, the lower handle portion 110 includes a depressible button or a push-button 702. Further, the sheath 104 within the upper handle portion 108 includes a groove 704 and the elongate member 114 (between the two handle portions) includes a corresponding protrusion 706. When an operator brings the upper and lower handle portions 108 and 110 together, and wishes to lock the handle 102 in this position, the operator may push the depressible button 702 which extends the protrusion 706 outward from the elongate member 114, engaging it in the groove 704 and locking the handle 102 in that position. At this stage, the operator may release the force applied on the handle 102, allowing her to efficiently utilize the end-effector unit 106 to perform the desired operation.

When the operator wishes to collapse the end-effector unit 108, she may release the depressible button 702, which retracts the protrusion 706 inwards, releasing the contact between the sheath 104 and the elongate member 114. The handle portions may then return to their normally spaced-apart position. FIG. 7A illustrates the handle 102 in the spaced apart position, while FIG. 7B shows the handle 102 in the locked position.

It will be understood that the number of protrusions and grooves may vary without departing from the scope of the present disclosure.

FIGS. 8A, 8B, and 8C illustrate another embodiment of a sample mechanical locking mechanism. This mechanism includes a protruding engaging member, such as a pin 802 on one handle portion (lower handle portion 110, for example), and a hook 804 on the other handle portion (upper handle portion 108, for example). The operator may bring the handle portions 108, 110 together and then lock them in position by engaging the hook 804 with the pin 802 as illustrated in FIGS. 8B and 8C. Both the locking mechanisms described with reference to FIGS. 7 and 8 are known in the art, and therefore they are not explained in detail here.

FIGS. 9A-9C illustrate another embodiment of the medical device 900. The previous embodiments of the medical device 900 included an end-effector unit present within the lumen. This particular embodiment of the medical device, however, presents a hollow sheath. This way, any tool or effector unit may be inserted through the handle and guided towards the distal end of the sheath without replacing the entire device.

The medical device 900 includes the handle 102 and the sheath 104. The handle 102 includes the upper handle portion 108, the lower handle portion 110, and a connecting portion, such as tube 902, between the upper and lower handle portions 108, 110. The proximal end of the sheath 104 is attached to the upper handle portion 108 and the proximal end of the tube 902 is attached to the lower handle portion 110. The distal end of the tube 902 is not connected to any member, but is movably mounted within the upper handle portion 108 and the sheath 104. In another embodiment, the tube 902 may be movable relative to the lower handle portion 110, but fixed relative to the upper handle portion 108. The diameter of the tube 902 is such that it may slide within the sheath 104 comfortably. Compliant member 112, such as a helical spring or an elastic sleeve may be disposed about the tube 902 to keep the upper and lower handle portions 108, 110 spaced apart. Application of a certain amount of force compresses the compliant member 112, pushing the tube 902 through the upper handle portion 108, and bringing the lower handle portion 110 closer to the upper handle portion 108.

The upper handle portion 108 and the lower handle portion 110 may include holes 904 and 906, respectively, along the longitudinal axis. In one embodiment, tube 902 passes through hole 904 of the upper handle portion 108, but is attached within the hole 906 of the lower handle portion 110, thereby substantially aligning the holes 904 and 906 longitudinally.

Any effector unit, tube, or other suitable medical device may be inserted in the medical device 900 through the hole 906. For example, a suction tube or a catheter may be guided through the handle 102 and the sheath 104 towards the operation site within a body. To accurately guide the inserted medical device towards the distal end of the sheath 104, the handle 102 may include a guiding mechanism.

To describe the guiding mechanism, in FIGS. 9A, 9B, and 9C, the end-effector unit is illustrated as a suction tube 908. It will be understood, however, that any other effector unit may be inserted and guided using this mechanism, without departing from the scope of the present disclosure. The suction tube 908 may be initially guided through the sheath 104 manually. Once the suction tube 908 reaches near the distal end of the sheath 104, however, accurate guiding and positioning may be required. For this positioning, the handle 102 may include certain engaging members, such as protrusions 910. It will be understood that the protrusions 910 may be barbs, annular protrusions, inflatable members or any other structure that can protrude into hole 906 to grasp or otherwise frictionally secure the suction tube 908 without deforming or damaging the suction tube 908. Moreover, the shape of the protrusions 910 may be conical, cylindrical, spherical, or any other such shape without departing from the scope of the disclosure. The function of the protrusions 910 is to hold the suction tube 908, enabling it to move along with the lower handle portion 110 when the lower handle portion 110 is pushed towards the upper handle portion 108.

In one embodiment, these protrusions 910 extend out of the inner surface of tube 902 only when the handle portions are moved toward each other. So, when the operator pushes the lower handle portion 110 toward upper handle portion 108, the protrusions 910 engage with the suction tube 908, moving the suction tube 908 distally in relation with the sheath 104. When the forces on the handle portions are removed, the protrusions 910 retract, leaving the suction tube 908 in the newly moved position, while retracting the tube 902 to its initial position. In this manner, the operator can accurately position any effector device, such as a suction tube, a catheter, and so on, at the operation site.

In case of angiographies and angioplasties, for example, the operator may first insert a catheter into an artery and then inject a dye to view any blockages in the artery. Then, using the same medical device, the operator may insert a stent into the blockages. To this end, the stent and the catheter may be supplied in the body through the medical device 900.

The device of FIGS. 1-9 may access a surgical site through an auxiliary access channel of an endoscope. The distal portion of the sheath 104 and the end-effector unit 106 may be inserted through a medical viewing instrument, such as a ureteroscope for viewing a surgical site during urologic surgery. The sheath 104 and the end-effector unit 106 may be received within an access channel of an endoscope such that the distal end of the sheath 104 (and end-effector unit 106) extends beyond the distal end of the endoscope. Therefore, actuation of the end-effector unit 106 can be viewed through the endoscope during a treatment procedure. In some embodiments, medical device 100 may be configured for insertion with the aid of a guidewire (not shown). For example, the sheath 104 may include a guidewire lumen (not shown) disposed on an outer surface thereof.

Upon insertion through an access channel of an endoscope, the medical device 100 can be moved relative to the endoscope. The sheath 104 may correspond in length to the length of the ureteroscope such that the distal ends of the two devices are substantially aligned during use.

Alternatively, the distal end of the sheath 104 may include one or more visualization markers (not shown), such as visible and non-visible markers; radiopaque markers; magnetic markers; ultrasonically reflective markers; and combinations thereof. With the help of a fluoroscope, ultrascope, or an endoscope, the operator may ascertain the exact location of the distal end of the medical device. Moreover, the markers help guide the medical device, through the body cavities, towards the operation site. The marker may be in the form of one or more rings around the distal end of the sheath, or any other shape without departing from the scope of the present disclosure.

The sheath 104 may also be used to provide electrical connection for end-effector units that require power to operate. An electrical wire connected to the end-effector unit may run along the length of the elongate member 114 or the sheath 104 and be connected to a battery module or an AC power connection provided in the lower handle portion 110.

In another embodiment, the sheath 104 may include multiple elongate members 114 or end-effector units 106. During urological medical procedures, the end-effector unit 106 may be positioned to grasp removable material from a surgical treatment site. Often, material grasped, such as a kidney stone, is too large to be removed from the site without breaking down the material first. A lithotriptor, which can include a laser fiber for directing energy to break down the material, may be concurrently introduced with the end-effector unit 106, which may also be used as a backstop during lithotripsy. The sheath 104 may also be used to introduce other medical devices such as ablation probes, lithotriptors, or cautery apparatus, so that these medical devices are also actuated when the end-effector unit 106 is actuated. For example, a laser probe and graspers may be positioned inside the lumen of the sheath 104, each attached to different elongate members.

FIG. 10 illustrates an additional embodiment of the present disclosure directed to a medical device handle 1002 for the relative movement of multiple end-effector units. The medical device 1000, as shown in FIG. 10, houses multiple end-effectors, such as a grasping end-effector unit 1004 for manipulating material within a patient's body and a device for breaking up material, such as a lithotriptor 1006.

As seen in FIG. 10, the medical device 1000 includes the handle 1002 and two sheaths 1008 and 1012, each with parts similar to the sheath in FIG. 1 (i.e., a lumen, a proximal end, and distal end). The lumen of the first sheath 1008 may include a basket 1004 attached to an elongate member 1010, the proximal end of which is connected to the lower handle portion 110. The lumen of the second sheath 1012 may include a lithotriptor 1006 attached to a second elongate member 1014, the proximal end of which is connected to the lower handle portion 110.

In one embodiment, by bringing the handle portions together, an operator may simultaneously actuate both end-effector units. In some situations, however, the operator may not require both the medical devices simultaneously. For these situations, the handle 1002 further includes a mechanism for selectively actuating only one end effector. In one embodiment, the handle 1002 may include a first button 1016 for the basket 1004 and a second button 1018 for the lithotriptor 1006. The elongate members 1010 and 1014 may be connected to a longitudinally movable surface (not shown) of the lower handle portion 110. This movable surface may travel between two positions—one at the top of the lower handle portion 110 (the effector unit 1004 is in this position) and the second at the bottom of the lower handle portion 110 (effector unit 1006 is in this position). The lower handle portion 110 below the movable surface may be substantially hollow, allowing the movable surface to move between the first and second positions.

When the corresponding button (such as the first button 1016) is depressed, the movable surface is placed in the first position, i.e., at the top. Now, when the handle portions are brought together, only the selected end-effector unit will extend distally out of the sheath, while the other end-effector unit does not extend beyond the distal end of the sheath (as shown in FIG. 10B).

It will be understood that this selective mechanism is merely exemplary and any other mechanism to selectively activate one end-effector may be utilized without departing from the scope of the present disclosure. Moreover, the number of end-effector units may not be restricted to only two. More end-effectors may be connected to the handle 1002 as required. Further, the attached medical devices may be detachably connected, so that the same handle may be utilized for one or more end-effectors, as required. For example, embodiments of the disclosed handle may be re-usable and therefore configured for repeated connection with disposable end-effectors.

The medical devices 1004 and 1006 may be inserted into an auxiliary access channel of a ureteroscope. Accordingly, handle 1002 allows for movement of both end-effector units 1004 and 1006 relative to the viewing area observed by the ureteroscope. In addition, movement of the upper and lower handle portions 108, 110 and the activation of the first and second buttons 1016, 1018 allow relative movement between the end-effector units housed within the medical device 1000.

In the embodiments described here and in the numerous other embodiments, the sheath diameter may vary between 5 FR to 15 FR. Preferably, the sheath diameter may be approximately equal to 10 FR. Moreover, the sheath may be rigid enough to provide better control for the operator, but at the same time flexible enough to easily maneuver within the patient's body.

Though shown with a retrieval device (and particularly a basket) and a lithotriptor device, the handles described above can be used with any other medical devices which require actuation or longitudinal positioning of medical devices at a treatment site. The reference to the use of a retrieval device and lithotriptor are used as examples and are not intended to limit the scope of the present disclosure.

Embodiments of the present disclosure may be used in any medical or non-medical procedure, including any medical procedure where removal of an object from within a body lumen is desired. In addition, at least certain aspects of the aforementioned embodiments may be combined with other aspects of the embodiments, or removed, without departing from the scope of the present disclosure.

Other embodiments of the present disclosure will be apparent to those skilled in the art from consideration of the specification and practice of the inventions disclosed herein. It is intended that the specification and examples be considered as exemplary only, with a true scope and spirit of the disclosure being indicated by the following claims.

What is claimed is:

1. A device comprising:
    a sheath including a distal end, a proximal end, and a first lumen and a second lumen extending therebetween;
    a first elongate member in the first lumen, the first elongate member including a distal end with an end-effector unit and a proximal end;
    a second elongate member in the second lumen, the second elongate member including a distal end that directs energy out of the second lumen; and
    a handle including a first handle portion connected to the proximal end of the sheath and a second handle portion connected to the proximal end of the first elongate member, the first and second handle portions being biased away from one another to contain the end-effector unit in the first lumen and moveable towards one another to extend the end-effector out of the first lumen.

2. The device of claim 1, wherein the end-effector expands when extended out of the first lumen.

3. The device of claim 2, wherein the end-effector is self-expandable.

4. The device of claim 2, wherein the second elongate member is a laser fiber, and the energy is a laser energy.

5. The device of claim 4, wherein the end-effector provides a backstop for the laser energy.

6. The device of claim 1, wherein the first elongate member is a suction tube.

7. The device of claim 1, wherein second elongate member is one of an ablation probe, a lithotriptor, or a cautery apparatus.

8. The device of claim 1, further comprising a mechanism on the handle operable to selectively direct the energy.

9. The device of claim 8, wherein the end effector is a grasping device and the second elongate member is a laser probe.

10. A system comprising:
    a scope including a distal end and at least one channel; and
    a device including:
        sheath including a distal end, a proximal end, and a first lumen and a second lumen extending therebetween;
        a first elongate member in the first lumen, the first elongate member including a distal end with an end-effector unit and a proximal end;
        a second elongate member in the second lumen, the second elongate member including a distal end that directs energy out of the second lumen; and
        a handle including a first handle portion connected to the proximal end of the sheath and a second handle portion connected to the proximal end of the first elongate member, the first and second handle portions being biased away from one another to contain the end-effector unit in the first lumen and moveable towards one another to extend the end-effector out of the first lumen,
    wherein a distal portion of the sheath is receivable in the at least one channel to place the distal end of the sheath at the distal end of the scope.

11. The system of claim 10, wherein the end-effector expands when extended out of the first lumen.

12. The system of claim 11, wherein the second elongate member is a laser fiber, and the energy is a laser energy.

13. The system of claim 10, wherein the distal end of the sheath is extendable beyond the distal end of the scope.

14. The system of claim 10, wherein the scope includes an imaging device and the end-effector is viewable with the imaging device when extended out of the first lumen.

15. The system of claim 10, wherein a length of the sheath is approximately equal to a length of the at least one channel.

16. A method comprising:
    placing a distal end of a device at a treatment site, the device including a sheath including a proximal end opposite of the distal end, a first lumen and a second lumen extending therebetween, and a first elongate member disposed in the first lumen, the first elongate member including an end-effector;
    grasping a handle of the device, the handle including a first handle portion connected to a proximal end of the sheath and a second handle portion connected to a proximal end of the first elongate member, the first and second handle portions being biased away from one another;
    moving the first handle portion towards the second handle portion to extend the end-effector out of the first lumen; and
    directing energy out of the second lumen.

17. The method of claim 16, wherein the device includes a mechanism on the handle for selectively directing the energy, and the directing step further comprises operating the mechanism.

18. The method of claim 16, further comprising placing a distal end of a scope at the treatment site, the scope including at least one channel, wherein the distal end of the device is placed at the treatment site when inserted into the at least one channel.

19. The method of claim 18, further comprising positioning the distal end of the device at or beyond a distal end of the at least one channel of the scope.

20. The method of claim 19, wherein the scope includes an imaging device, and the method further comprises viewing the end-effector with the imaging device before directing the energy.

* * * * *